United States Patent [19]

Hasslinger

[11] 4,396,013

[45] Aug. 2, 1983

[54] SUPPORT AND GUIDE STRAP

[75] Inventor: Russell Hasslinger, Wyckoff, N.J.

[73] Assignee: Velcro USA Inc., New York, N.Y.

[21] Appl. No.: 212,548

[22] Filed: Dec. 3, 1980

[51] Int. Cl.$^3$ .............................................. A61F 13/00
[52] U.S. Cl. .................................... 128/133; 128/134
[58] Field of Search ............................... 128/133, 134

[56] References Cited

U.S. PATENT DOCUMENTS

| | | | |
|---|---|---|---|
| 2,668,577 | 2/1954 | Vanderschel | 128/134 |
| 2,717,437 | 9/1955 | de Mestral | |
| 2,766,751 | 10/1966 | Topa | 128/134 |
| 3,009,295 | 11/1961 | Seidel et al. | |
| 3,399,670 | 9/1968 | Veasey | 128/134 |
| 3,487,474 | 1/1970 | De Meo | |
| 3,570,495 | 3/1971 | Wright | |
| 3,872,860 | 3/1975 | Noblitt | |
| 4,004,583 | 1/1977 | Johnson | |
| 4,108,170 | 8/1978 | Spann | 128/134 |
| 4,211,218 | 7/1980 | Kendrick | 128/134 |

Primary Examiner—Kyle L. Howell
Assistant Examiner—C. W. Shedd
Attorney, Agent, or Firm—Pennie & Edmonds

[57] ABSTRACT

A strap (10) adapted for encircling securement about the midsection of an individual including a pair of handles (38) whereby an attendant may assist both supporting and guiding the individual during ambulatory movement. The strap includes a first length (12) having a base layer (16) and first engaging elements (18). A second length (14) likewise formed of a base layer is connected to an end of the first length. The first and second lengths comprise minor and major portions of the strap, respectively. A fastener member (26) having a backing and second engaging elements (30) which mate with the first engaging elements is disposed at the end of the second length remote from the connection with the first length. The handles are carried by the second length to be disposed to the rear (FIGS. 4 and 5) when the first and second engaging elements are engaged for securement of the strap on the individual. A layer of backing material (22) extends along the second length and when the strap is so engaged for securement, the backing material is disposed toward the individual providing the strap with a non-slip characteristic. Both the base layer and handle are of sturdy and pliant nature, while the engaging elements may comprise a VELCRO fastener.

9 Claims, 5 Drawing Figures

U.S. Patent  Aug. 2, 1983  4,396,013
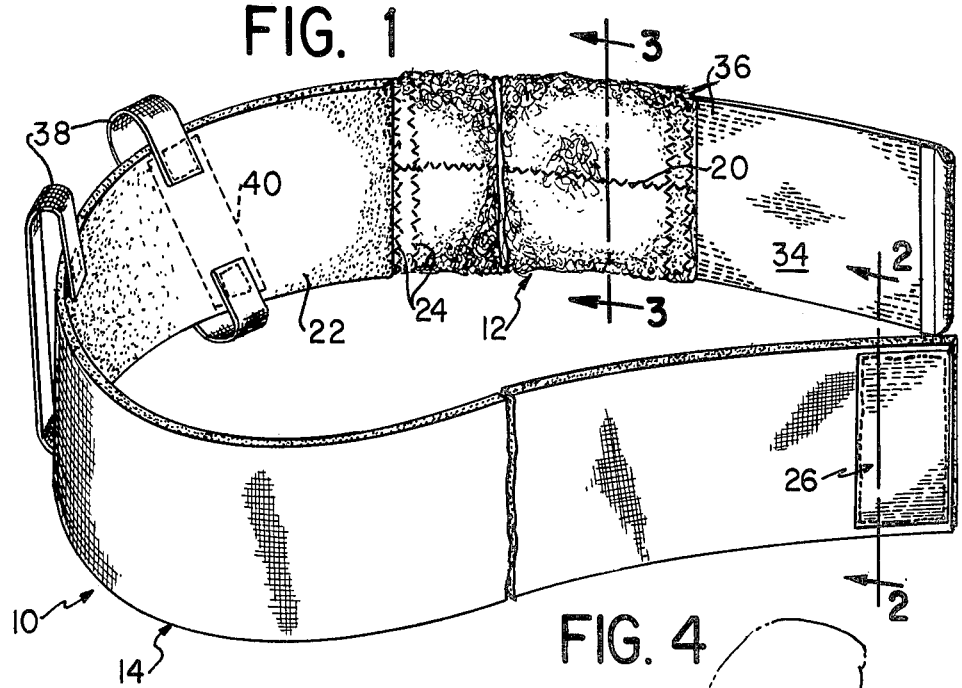
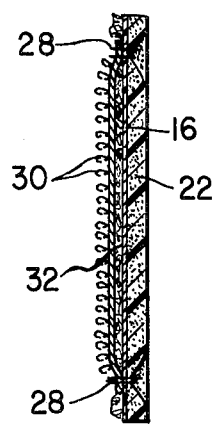
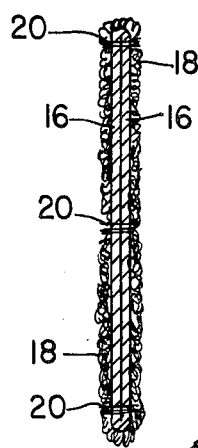
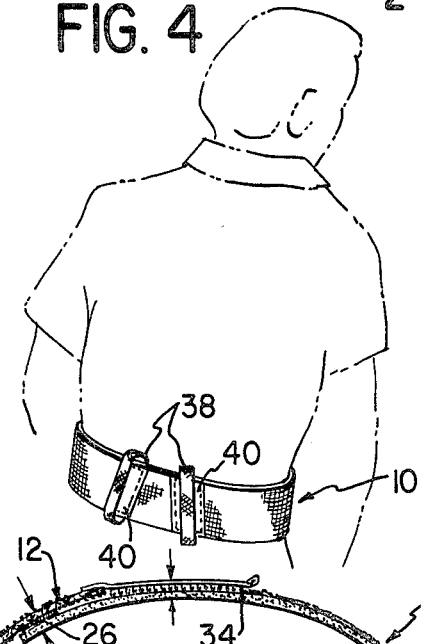
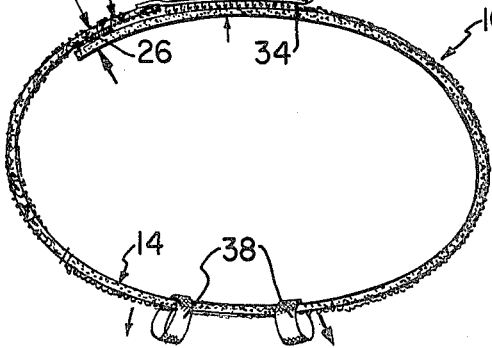

SUPPORT AND GUIDE STRAP

TECHNICAL FIELD

The present invention relates to a strap adapted to be placed around the trunk of the body, such as within the region of the midsection of an individual capable of ambulation, and having a handle to be gripped by an attendant to assist both in supporting and guiding the individual during ambulatory movement.

BACKGROUND ART

Straps and belts adapted to be placed around the trunk of the body as well as around a body appendage are known to the prior art. One such device is the tourniquet disclosed in U.S. Pat. No. 3,570,495 to F. O. Wright. The tourniquet utilizes a form of fastener having hook components on a base fabric capable of mating interaction with, upon placement of the hook components on, a base fabric carrying a multiplicity of loops to resist, after engagement, separation along the plane parallel to the interfacial plane of engagement. The hook components and loops, however, are readily separable merely by a peeling force applied substantially normal to this interfacial plane. This type of fastener generally is formed of a sheet of synthetic woven or knitted fabric having raised threads of synthetic material, such as nylon. The threads are either napped or unnapped and provide a pile surface defined by a plurality of loops which may be thermally treated to a semi-rigid state. Certain of the loops may then be cut along one side near their outer extremity to form hooks. Such a fastener is marketed by Velcro Corporation, New York, New York, under the registered trademark VELCRO brand hook-and-loop fasteners. The fastener has gained wide acceptance because of the properties of the hooks and loops which permit the mating engagement and both the degree of securement and releasing capability, as previously described. Reference may be had to U.S. Pat. Nos. 2,717,437 and 3,009,235 to G. de Mestral for further description and particulars.

The tourniquet of Wright is adapted to be placed on an appendage of the body and secured in place by a VELCRO fastener. The substrate supporting the VELCRO fastener, once the tourniquet is so located, is pressurized for whatever medical procedure is contemplated.

The prior art also includes U.S. Pat. Nos. 3,872,860 to N. L. Noblitt and 4,004,583 to D. E. Johnson. The Noblitt patent discloses a belt described as a pelvic traction belt adapted to be placed around the trunk of the body. The belt includes an outer face formed of a woven fabric having a plurality of catch-defining external loops. A strap is described as being fastened to the belt by interaction of the external loops of the belt and hook parts of the strap. The strip is subject to be placed under a tensioning load. Noblitt characterized the fastener including the loops and hooks as a VELCRO fastener. The Johnsom patent discloses a strap, utilized as a restraining device for restraining the movement of an individual. The restraining device is illustrated as applied to the upper trunk or the body and to the legs to accomplish this end. The restraining device includes a VELCRO fastener.

A further patent of the prior art is U.S. Pat. No. 3,487,474 to A. J. De Meo. The De Meo patent discloses a belt connected at the front by a buckle-type arrangement including, also, loops and a fastening strap, and having a pair of handgrips carried by the belt substantially within the region midway of the buckle-type arrangement.

The De Meo device, among possible others of like nature, includes bulky and heavy hardware making the belt both cumbersome and uncomfortable to wear; and, in addition, the arrangement on the belt of De Meo is difficult to manipulate both for securement in a body embracing condition and in release from that condition. This difficulty would be even more pronounced if the belt were to be used with invalid patients. Further, the number of adjustable, preselected positions in use of the De Meo device is limited requiring a plurality of different sized belts. As may be apparent, the cost to manufacturers in the production and supply of belts of different size and/or dimension is greater than would be the cost of a belt having greater versatility of use.

This latter disadvantage of the De Meo structure applies in some degree to the devices of the prior art, also described above, and each of the prior art structures have the disadvantage that their construction renders them relatively inflexible, stiff and uncomfortable in use. They are, also, in physical makeup, rather dense in cross-section with little or no capability of "breathing". This factor only compounds the feeling of uncomfortability in use.

Further, the Wright, Noblitt and Johnson devices neither have a capability for the support and guiding of an individual nor are they considered to be versatile in use. These prior art devices, either because of the manner of fastening or because of their constructional makeup, are of a nature that they are uncomfortable in use.

A further device of the prior art is adapted for use as a strap both for the support and guiding of an individual. The strap is adapted to be placed about the body, within the region of the midsection, and secured by face-to-face engagement of a plurality of elements of the hook-and-loop type supported in upstanding relation along a surface of a base layer and a plurality of engaging elements carried by a fastener member at the overlapped end of the strap. The strap is of double ply construction, that is, the base layer which is of knit material is doubled over or folded upon itself, whereby the engaging elements of the hook-and-loop type are supported along both surfaces. A second fastener member is located adjacent the other strap end, on the opposite side of the strap from the first-mentioned fastener member; and a handle in the form of a web of pliant, yet sturdy material is secured to a surface which shall be the outer surface when the strap is so located. The handle is secured at spaced locations along the length of the strap and gripped by an attendant in assisting or aiding ambulation.

While this last-mentioned strap may overcome substantially those problems and disadvantages of the prior art devices mentioned theretofore, such as bulkiness, difficulty in manipulation, and lack of total adjustability, among other, the strap, itself, suffers from certain problems and disadvantages. Thus, the double ply knit material makeup has little or no holding capability against slippage around the body. Further, the handle which is secured along the length of the strap has been found somewhat wanting with regard to the measure of control that the attendant is able to provide.

DISCLOSURE OF INVENTION

The present invention is directed to a strap both for support and guiding (hereafter discussed as a "strap") has a particular adaptation in use by an ambulatory patient. The strap, not unlike the strap of the prior art, last-mentioned, is adapted to be placed about and removed from the trunk of the body of an ambulatory patient within the region of the midsection to assist both in the support and guiding movement of the patient. While the strap of the present invention may be seen to have a degree of similarity to that strap, it will be apparent from the discussion to follow that the present strap clearly distinguishes thereover and over the other prior art devices in several important respects.

The strap is comprised of a web including a base layer which is lightweight, and of a soft, cushioning nature capable of "breathing". The base layer, further, is pliant and capable of flexing in accordance with movements of the body. The major length of the strap is comprised of the base layer and a coextensive cushioning layer; while a minor length of the strap, connected to the major length, is comprised of the base layer which is folded upon itself to provide a double ply of material.

As an important aspect of the invention, the base layer supports a plurality of engaging elements of the hook-and-loop type in upstanding relation along at least one surface. A fastener member is positioned on the strap adjacent an end of the major length remote from the connection with the minor length. The fastener member is comprised of a backing and carries a plurality of engaging elements adapted to mate with the engaging elements of hook-and-loop type carried by the base layer. The strap is of a length sufficient to encircle completely the midsection of the individual and of a width so that a substantial area of strap is in contact with the body or with the apparel worn by the individual. As desired, a second fastener member, likewise comprised of a backing and a plurality of engaging elements adapted to mate with the engaging elements of hook-and-loop type, may be located within the minor length of the strap, such as within a region spaced from the connection with the major length. The second fastener, however, will be located on the side of the strap opposite from that upon which the first-mentioned fastener member is located. Thus, without comprising versatility of usage of the strap, an enhanced measure of securement may be obtained.

As a further important aspect of the invention, a pair of handles are carried by the strap in a position such that each handle will be disposed to the rear of the individual when the strap is placed and secured in the manner heretofore described. Each handle is formed by an elongated member comprising a web of pliant, yet sturdy material, and preferably of a width thereby to permit the handle to be gripped. The opposite ends of each handle are secured to the strap and the handles provide assistance for both the support and guiding movement of the individual by an attendant. As a further feature, each handle upon an application of guiding and supporting manipulation by the attendant serves to create a stronger than normally expected closure and increased resistance to separation of the engaging elements through forces acting in shear or parallel to the interfacial plane engagement. The stronger than expected closure is an incident of the action-reaction forces acting between the midsection of the individual and the strap. These forces develop substantially contemporaneously with the guiding and supporting manipulation of the handle by an attendant.

As a still further aspect of the invention, a tab including a backing and a plurality of engaging elements is attached to the overlapping end of the strap. The engaging elements will extend in the direction of the engaging elements of the second fastener member, if the second fastener member is used. The strap of the present invention may be rapidly attached and released from the trunk of the body. It provides for adjustment, thereby to be versatile, and it is comfortable in use. The combination of a strap having handles permits in assisting both support and guiding movement of the individual by an attendant and, when secured by the engaging elements, contemporaneously serves in development of action-reaction forces acting between the midsection of the individual and the strap to create a stronger than normally expected closure and increased resistance to separation of the engaging elements.

These and other advantages of the present invention will become abundantly clear as the description continues.

BRIEF DESCRIPTION OF DRAWING

FIG. 1 is a perspective view of the support and guide strap of the invention;

FIG. 2 is a view in section as seen along the line 2—2 in FIG. 1;

FIG. 3 is a view in section as seen along the line 3—3 in FIG. 1;

FIG. 4 is a perspective view of the strap placed around the midsection of an individual;

FIG. 5 is a plan view of the strap illustrating resultant forces on the strip as an incident to both support and guiding manipulation and exertion of body muscles.

BEST MODE FOR CARRYING OUT THE INVENTION

The strap of the present invention, generally depicted by the numeral 10, comprises a length 12 which may be characterized as a first length and a length 14 which may be characterized as a second length. Each length includes a base layer 16 having a plurality of engaging elements upstanding from one surface thereof. The engaging elements are of the hook-and-loop type, such as the heretofore described VELCRO ® brand loop fastener. The engaging elements, as perhaps best illustrated in FIG. 3, are denoted by the character "18". As may also be seen in the Figure, the base layer of the first length is folded upon itself to provide a double ply. The doubly ply serves both to reinforce and provide a measure of cushioning for wearing comfort when the strap is secured about the individual. The base layer preferably is lightweight and pliant and may be woven or knitted to provide a capability of "breathing" to further enhance wearing comfort and cushioning.

The folded portions of the base layer 16 of the first length are joined together by any known process as, for example, by sewing. A plurality of seams 20 may be seen in FIG. 3 and include the seams located in the vicinity of and along the marginal edges created by each fold, as well as the seams located on each side of the junction between abutting edges of the base layer.

The first length 12 of double ply base material comprises only a minor length of the strap 10. To this end, the first length which serves in the fastening of the strap in a body encircling disposition need be only as long as required to accomplish the securing function, yet provide the strap with a satisfactory measure of adjustment capability.

As previously indicated, the base layer 16, among other characteristics, has a capability of "breathing". However, it has been found that that capability suffers to a great extent when the base layer is folded to the double ply construction of the prior art. This factor and others are taken into consideration in determining the minor length. Thus, the length should be sufficient to provide a surface area for securement, as will be described, all the while considering a capability of use within some range of midsection measurement and not so long thereby to induce discomfort resulting from a reduction in "breathing" capability.

A particularly important aspect of the present invention is in the construction of the second length 14 which comprises the major length of strap 10. The second length comprises a base layer 16, as previously discussed, although of only a single ply, and a layer 22 of backing material, such as foam. The base layer 16 and foam layer 22 are coextensive and the layers may be joined together in the manner as discussed, that is, by sewing a plurality of seams, or the layers may be adhered together by any type of adhesive commonly employed for this purpose.

This construction identifies a product of the assignee of the present invention as "VELFOAM LOOP/3301".

The knit material and foam backing of the second length provides sufficient "breathing" capability so that the strap does not reduce the measure of comfort, and the foam backing enhances the wearability of the strap by increasing the cushioning effect over and above the level of cushioning derived from the double ply of material of the prior art strap. Further, the foam backing provides the strap with a relatively slip-free characteristic, not obtainable with the prior art strap of double ply construction.

The two lengths, that is the major and minor lengths, preferably are joined together by sewing one or more seams 24 to provide a secure junction.

The strap 10 may be of any width to provide to significant surface-to-surface contact with the body or with the apparel to be worn by the individual in assisting both guiding and supporting manipulation. The wider the strap the greater the area of distribution of the forces resulting from the manipulation between the strap and the body. A wider width of strap, also, will assist in the prevention of binding irritation which may result from a strap of narrower width. The overall length of strap may vary in increments, for example, of one-half foot, thereby to be accommodated to a host of individuals of different girth. The width of the strap may be approximately four inches in adult sizes. The major and minor lengths will vary individually according to the total length.

A fastener member 26 in the form of a backing is located at the end of the second length 14 remote from the junction of the two lengths. The backing may be secured both to the base layer 16 and overlying foam layer 22 by conventional techniques, as by sewing a seam 28 along the perimeter of the backing. The seam, thus, extends through both the base layer and foam layer as may be seen in FIG. 2. The backing carries substantially throughout its surface area a plurality of engaging elements adapted to mate with the engaging elements 18. These engaging elements may be of hook type, such as the heretofore described VELCRO ® brand hook fastener. The engaging elements, perhaps best illustrated in FIG. 2, are denoted by the character "30". It is, additionally, contemplated that the engaging elements 30, rather than of the classical hook-type configuration, may take a mushroom-like configuration for engagement with engaging elements 18 of loop configuration.

The fastener member 26 includes a base 32 of a sturdy, yet pliant material. And, the plurality of engaging elements 30 extend upwardly from the base forming a pile surface positionable for interengagement with the engaging elements 18. The strap may be releasably secured in an encircling relation at the midsection of the trunk of the individual in a snug, firm, and adjustable manner by moving the first member into contact with the second member. To this end, the second member carried at the end of the major length assumes a body encircling position and the first member is moved into contact with the second member. Contact is through releasable meshing engagement of the engaging elements 18 and 30, as illustrated in FIG. 5. Fastener member 26 may be releasably engaged, as described and illustrated in FIG. 5, in a host of different longitudinal positions along the minor length. Thus, the supporting strap 10 is accommodated to a number of individuals of different girth.

A tab 34 is carried at the end of the overlapping length of the strap 10. The tab carries engaging elements 36 of a type similar to those of the engaging elements of fastener member 26. As apparent, however, the engaging elements on both the tab and fastener member are oppositely directed. The engaging elements 36 provide additional engagement with the engaging elements 16 and increased resistance to separation of all engaging elements upon the development of forces acting parallel to the interfacial plane of engagement.

A pair of handles 38 each in the form of an elongated member are secured at opposite ends to strap 10 within the major length. As may be seen to advantage in FIG. 1, the opposite ends of each handle are folded around the edges of the strap and each handle is secured to the strap by a plurality of seams of sewing in the region of the ends. A backing 40 preferably is sewn to the strap in a position below each handle. The backing provides support for the seams and substantially assures positive securement of the handles along the strap.

The handles are secured in spaced dispositions along the strap, although generally at the midpoint of its length so that the handles will be located within the region of the individual's spine when the strap is used. Further, the handles may be inclined slightly, as best seen in FIG. 5. The incline of the handles will enable the handles to be gripped by an attendant with greater leverage in the guiding and supporting of the individual while the attendant walks to the rear. To assist in gripping, each handle preferably is of a width substantially less than that of the width of the strap, for example, one inch. Each handle, further, is pliant and sturdy in nature. The backings may be of similar material, likewise to display those characteristics.

As an important aspect of the invention, and as may be seen to advantage in FIG. 5, during the guiding and supporting of the individual, the attendant normally will pull on the handles 38 thereby to develop the resultant forces illustrated by the directional arrows at the handles. Further, the individual will develop the generally oppositely directed forces in reaction also as illustrated by the directional arrows within each of the areas of engagement of the engaging elements along the overlapping length of the strap. These forces and the forces through manipulation of the strap by the attendant comprise action-reaction forces which, in use of the strap, provide a substantial degree of securement and increased resistance to separation of all engaging elements. Nevertheless, the strap may be readily removed from a secured position with little or no additional peeling effort.

By reason of the foregoing construction, an improved strap has been provided. The strap is of a size and formed in a manner to enhance comfort when it is worn, it is versatile in its application to individuals having varying girth, it may be placed about and removed readily from the individual, and it provides positive control during movement. Because of the development of action-reaction forces between the individual and strap, a substantial degree of securement is provided as is increased resistance to the separation due to the direction of the action-reaction forces. An even stronger than normal closure, with litlle or no affect upon the manner of removal of the strap, is created.

Having described the invention with particular reference to the preferred form thereof, it will be obvious to those skilled in the art to which the invention pertains after understanding the invention, that various changes and modifications may be made therein without departing from the spirit and scope of the invention as defined by the claims appended hereto.

I claim:

1. A strap for assisting both in guiding and supporting an individual comprising an elongated member in the form of a base layer having an overall length sufficient to permit complete overlapping encirclement of the midsection of said individual and an overall width so that said strap when used is superposed substantially only within the region of the waist, first means at one end of said base layer carrying first engaging elements of the hook-and-loop type, second means at the other end of said base layer carrying second engaging elements adapted to mate with said first engaging elements adapted to mate with said first engaging elements in a releasably secure, snug fitting, selective engagement when said elongated member is encircled around said midsection, one of said ends is moved to overlap the other end and then moved to allow said first and second engaging elements to matingly interact, handle means in the form generally of a pair of members to be gripped, each said member secured to said base layer at spaced-apart locations along its length, on the surface away from the body at locations spaced substantially equidistantly from the ends of said base layer and in an orientation inclined with respect to a vertical axis whereby said handle means may be gripped with greater leverage, said members when said strap is in overlapping encirclement being disposed to the rear of said individual thereby with said greater leverage providing a capability for guiding and supporting said individual, the contemporaneous development of action-reaction forces between said elongated member and the midsection of said individual and a substantial degree of securement of said elongated member in said releasably secured position by increased resistance to separation of said first and second engaging elements due to the direction of said action-reaction forces, and backing means carried along at least a length of said base layer on the surface adjacent the body of said individual when said strap is releasably secured, said backing means providing substantially a non-slip surface thereby to maintain the positional location of said elongated member when releasably secured around said midsection.

2. The strap of claim 1 wherein said first means comprises said base layer doubled along its length so that said first engaging elements are carried on both surfaces, said first engaging elements disposed in upstanding relation relative to said surface.

3. The strap of claim 1 or 2 wherein said base layer has a plurality of third engaging elements of the hook-and-loop type along the surface opposite said backing means, both said third engaging elements and backing means extending from said first means to the other end of said base layer.

4. The strap of claim 3 wherein said second means includes a base member carrying said second engaging elements; said base member disposed on the surface opposite said backing means.

5. The supporting strap of claim 4 further including a tab, said tab connected to said one end of said base layer and having fourth engaging elements adapted for mating with said third engaging elements providing additional releasable securement of said strap.

6. The supporting strap of claim 1 wherein said base layer is comprised of a pliant, porous material and said backing means is comprised of a foam material to enhance the cushioning characteristic of said elongated member and not deleteriously affect air circulation whereby wearing comfort is enhanced.

7. A strap for assisting both in guiding and supporting an individual, which strap comprises an elongated member in the form of a base layer of an overall length sufficient for complete overlapping encirclement by said strap of the midsection of said individual and of an overall width so that said strap in used is superposed substantially only within the region of the waist, first means comprising a minor length of said base layer carrying first engaging elements of the hook-and-loop type doubled along its length so that said first engaging elements are carried on both surfaces, second means at the other end of said base layer including a base member carrying said engaging elements adapted to mate with said first engaging elements in a releasably secure, snug fitting, selective engagement when said elongated member is encircled around said midsection, one of said ends is moved to overlap the other end and then moved to allow said first and second engaging elements to matingly interact, handle means in the form generally of a pair of gripping members, each said gripping member secured to said base layer at spaced-apart locations along its length, on the surface away from the body at locations spaced substantially equidistantly from the ends of said base layer and in an orientation inclined with respect to a vertical axis whereby said handle means may be gripped with greater leverage, said gripping members when said strap is in overlapping encirclement being disposed to the rear of said individual to provide a capability both for guiding and supporting said individual, the contemporaneous development of action-reaction forces between said elongated member and the midsection of said individual and a substantial degree of securement of said elongated member in said releasably secured position by increased resistance to separation of said first and second engaging elements due to the direction of said action-reaction forces, and backing means comprised of a foam material carried by said base layer within the major length and on the surface adjacent the body of said individual when said strap is releasably secured, said backing means providing substantially a non-slip surface thereby to maintain the positional location of said elongated member when releasably secured around said midsection.

8. The strap of claim 7 wherein said base layer has a plurality of third engaging elements of the hook-and-loop type on the surface opposite said backing means, both said third engaging elements and backing means extending from said first means to the other end of said base layer, and said second engaging means, also, disposed on the surface opposite said backing means.

9. The strap of claim 8 further including a tab, said tab connected to said one end of said base layer and having fourth engaging elements adapted for mating with said third engaging elements providing additional releasable securement of said strap.

* * * * *

UNITED STATES PATENT AND TRADEMARK OFFICE
CERTIFICATE OF CORRECTION

PATENT NO. : 4,396,013

DATED : August 2, 1983

INVENTOR(S) : Russell Hasslinger

It is certified that error appears in the above-identified patent and that said Letters Patent is hereby corrected as shown below:

On the title page under References Cited U.S. Patent Documents "3,009,295 to Seidel et al. should be --3,009,235 to de Mestral--.

In Column 2, line 62, "other" should be --others--.

In Column 7, line 20, "litlle" should be --little--.

Signed and Sealed this

Twenty-second Day of November 1983

[SEAL]

Attest:

GERALD J. MOSSINGHOFF

Attesting Officer

Commissioner of Patents and Trademarks